United States Patent
Steinhardt

(10) Patent No.: US 7,087,369 B2
(45) Date of Patent: Aug. 8, 2006

(54) CORNEA PRESERVATION MEDIUM

(75) Inventor: Richard A. Steinhardt, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 459 days.

(21) Appl. No.: 10/738,331

(22) Filed: Dec. 17, 2003

(65) Prior Publication Data

US 2005/0136391 A1  Jun. 23, 2005

(51) Int. Cl.
*A01N 1/00* (2006.01)

(52) U.S. Cl. ........................................ 435/1.1
(58) Field of Classification Search ............. None
See application file for complete search history.

(56) References Cited

U.S. PATENT DOCUMENTS

| | | |
|---|---|---|
| 5,024,947 A | 6/1991 | Inlow et al. |
| 5,045,454 A | 9/1991 | Bertheussen |
| 5,438,041 A | 8/1995 | Zheng et al. |
| 5,688,529 A | 11/1997 | Lidgate et al. |
| 5,824,322 A | 10/1998 | Balasubramanian |

*Primary Examiner*—Sandra E. Saucier
(74) *Attorney, Agent, or Firm*—Richard Aron Osman

(57) ABSTRACT

Steinhardt defined medium preserves cornea tissue during cold storage. Tissue preservation kits comprise a premeasured amount of Steinhardt's medium and copackaged instructions describing use of the medium to preserve a tissue. Kits for making Steinhardt medium comprise premeasured amounts of medium ingredients; and copackaged instructions describing how to combine the ingredients to make the medium. The medium is made by combining the recited ingredients, and used by incubating a tissue in the medium.

13 Claims, No Drawings

CORNEA PRESERVATION MEDIUM

This work was supported by National Institutes of Health Grants AR44066 and EY 13436. The U.S. government may have rights in any patent issuing on this application.

FIELD OF THE INVENTION

The field of the invention is a cornea tissue preservation medium.

BACKGROUND OF THE INVENTION

We have previously disclosed that the mechanism of cell membrane repair requires an active process of calcium regulated exocytosis (Steinhardt R A, Bi G, Alderton J M. *Cell Membrane Resealing by a Vesicular Mechanism Similar to Neurotransmission. Science* 1994; 263: 390–393). This lead to our idea that membrane breaks could be repaired by artificial means under conditions where normal metabolism is curtailed, such as the storage of donated tissues for transplantation.

We have devised a new corneal preservation medium and tested it against the American standard, Optisol GS (Bausch & Lomb). Optisol was developed for low temperature storage of corneas and other eye tissues by Richard L. Lindstrom and Debra Skelnik (U.S. Pat. Nos. 5,104,787; 5,407, 669). This tissue preservation solution was originally marketed by Chiron Ophthalmics, Irvine, Calif. Bausch & Lomb acquired Chiron Corp.'s vision-care product line in 1997. Optisol GS is commercially available from: Bausch & Lomb Surgical, Inc. (San Dimas, Calif.)

Relevant Literature

Togo T, Alderton, J M, Bi G, Steinhardt R A. The mechanism of facilitated cell membrane resealing. Journal of Cell Science 1999; 112: 719–731; Togo T, Krasieva T B, Steinhardt R A. A Decrease in Membrane Tension Precedes Successful Cell-Membrane Repair. Molecular Biology of the Cell 2000; 11: 4339–4346; Bi G, Morris R L, Liao G, Alderton J M, Scholey J M, Steinhardt R A. Kinesin- and Myosin-driven Steps of Vesicle Recruitment for $Ca^{2+}$-regulated Exocytosis. The Journal of Cell Biology 1997; 138(5): 999–1008).

SUMMARY OF THE INVENTION

The invention provides methods and compositions for preserving tissue, particularly corneal tissue for cold storage and transplantation. In one embodiment, the invention provides Steinhardt medium, a tissue preservation medium comprising in sterile solution ingredients in final concentration:

potassium sulfate $K_2SO_4$ (5 mM)
L-aspartic acid (110 mM)
magnesium sulfate (1.2 mM)
calcium hydroxide (2.0 mM)
potassium phosphate monobasic $KH_2PO_4$ (20 mM)
N-2-hydroxyethylpiperazine-N'-2-ethanesulfonic acid (HEPES) (5 mM)
ethylenediaminetetraacetic acid (EDTA) (1 mM)
taurine (20 mM)
zinc sulfate (1 microM)
N-(tert-butyl) hydroxylamine HCL (200 microM)
dextran M.W. 60,000–90,000 (5.5% w/v)
N-acetyl-cysteine (0.5 mM)
gentamycin sulfate (0.02% w/v)
creatine phosphate (5 mM)
Lipid Concentrate (GIBCO/INVITROGEN #11905-031) (1% v/v) at pH adjusted to 7.45 with 1 M KOH, and having an osmolarity of 310 to 320 mOsmoles.

In other embodiments, the invention provides kits for preserving tissue including:

kits comprising a premeasured amount of the disclosed preservation medium;

kits comprising a premeasured amount of the disclosed preservation medium, and recorded instructions copackaged or associated with the premeasured amount describing use of the medium to preserve a tissue; and kits for making the disclosed medium comprising premeasured amounts of the ingredients, or a plurality of the ingredients; and recorded instructions copackaged or associated with the premeasured amounts describing how to combine the ingredients to make the medium.

The invention also provides methods of making the disclosed medium, comprising the step of combining the recited ingredients to make the medium; and methods of using the disclosed medium comprising incubating a tissue in the medium, preferably cornea tissue, preferably at 4 degrees C., and preferably for at least 7 days, typically not more than 21 days. The incubating step is typically followed by an assessment of post-incubation survival utility to determine whether the tissue has retained its suitability for its intended use, typically transplantation.

DESCRIPTION OF PARTICULAR EMBODIMENTS OF THE INVENTION

The invention provides methods and compositions for preserving tissue, particularly corneal tissue for cold storage and transplantation. In one embodiment, the invention provides Steinhardt medium, a unique tissue preservation medium based on fundamental physiological principles and on research findings from our laboratory regarding maintenance of cell membrane integrity. After testing many different iterations, we have established a particular formulation that provides exceptional tissue preservation of a panel of human and large animal organs and tissues, including cornea, kidney and heart tissue. The medium is typically provided in sterile solution; the ingredients and their final solution concentrations recited above. More detailed descriptions of the ingredients and their respective functions are described below.

The ionic composition of Steinhardt medium is designed to approximate intracellular ionic composition for potassium, sodium, and magnesium ions.

The HEPES (SIGMA #H-9136)(N-2-Hydroxyehtylpiperazine-N'-2-ethanesulfonic acid) provides a physiologically compatible buffer widely used in cell culture media. The potassium salts of the sulfate ion ($K_2SO_4$) and the monobasic phosphate ion ($H_2PO_4$) are used in place of the sodium salts of these ions that are typically used in cell culture media.

L-aspartic acid is provided based on observations in our laboratory that cells microinjected with solutions containing high concentrations of the potassium salt of L-aspartic acid continue to grow and divide. L-aspartic acid is a key amino acid in cellular metabolism that links the urea cycle to the citric acid cycle. Steinhardt medium uses 110 millimolar L-aspartic acid to yield 110 millimolar aspartate. 13 millimolar aspartate has been used in cardioplegia (Rosenkranz et al., Journal of Thoracic Cardiovascular Surgery 1986; 91: 428–435).

Potassium hydroxide is used to adjust the pH, causes the acids such as L-aspartic acid and ethylenediaminetetraacetic acid (EDTA) to dissolve, and also provides high potassium ion levels characteristic of the intracellular environment.

The chelator ethylenediaminetetraacetic acid (EDTA) is used to buffer the level of calcium, magnesium, and zinc ions. Extracellular free calcium ion at about 1 millimolar and free magnesium ion at about 1.2 millimolar result in optimal cell membrane repair (Steinhardt R A, Bi G, Alderton J M. Cell Membrane Resealing by a Vesicular Mechanism Similar to Neurotransmission. Science 1994; 263: 390–393). This paper demonstrates that cell membrane repair is an active biological process that requires calcium-dependent exocytosis of vesicles at the cell membrane. Excessive free magnesium ion antagonizes the vesicle exocytosis and membrane resealing. EDTA also chelates trace amounts of iron and copper that may be present in the medium. Iron and copper are known to be catalytic for free radical reactions that are damaging to cells (Evans et al. Catalytic Metal Ions and the Loss of Reduced Glutathione from University of Wisconsin Preservation Solution. Transplantation 1996; 62(8): 1046–1049)

The zinc ion is an essential cofactor for DNA repair and other enzymatic cellular processes (Chimienti F, Aouffen M, Favier A, Seve M. Zinc homeostasis-regulating proteins: new drug targets for triggering cell fate. Current Drug Targets 2003; 4(4):323–38).

The amino acid taurine is cytoprotective (Eppler B, Dawson R Jr. Cytoprotective role of taurine in a renal epithelial cell culture model. Biochemical Pharmacology 2002; 63: 1051–1060). It is an abundant intracellular amino acid and provides multiple homeostatic functions (Lourenco et al., Taurine: a conditionally essential amino acid in humans? An overview in health and disease. Nutr Hosp. 2002;17(6): 262–70).

The 5.5% dextran is consistent with the corneal preservation medium described by McCarey B E and Kaufman H E. Improved Corneal Storage. Investigative Ophthamology 1974; 13(3): 165–173; and U.S. Pat. No. 5,370,989. Optisol GS contains 1% dextran. The dextran used has an average molecular weight between 64,000 and 76,000.

The N-acetyl-cysteine is a cell permeable precursor of glutathione. (Ceconi C, Curello S, Cargnoni A, Ferrari R, Albertini A, Visioli O. The role of glutathione status in the protection against ischemic and reperfusion damage: effects of N-acetyl cysteine. Journal of Molecular and Cellular Cardiology 1988; 20(1): 5–13). The 0.5 mM concentration is consistent with that used in U.S. Pat. No. 5,370,989.

N-tert-Butyl hydroxylamine is an antioxidant that prevents free radical-induced toxicity to mitochondria (Liu J, Atamna H, Kuratsune H, Ames B N. *Delaying brain mitochondrial decay and aging with mitochondrial antioxidants and metabolites. Ann N Y Acad Sci.* 2002; 959:133–66). Also, Atamna et al. *N-t-Butyl hydroxylamine is an antioxidant that reverses age-related changes in mitochondria in vivo and in vitro. FASEB J.* 2001;15(12):2196–204; also, U.S. Pat. No. 6,455,589. N-t-butyl hydroxylamine, a hydrolysis product of alpha-phenyl-N-t-butyl nitrone, is more potent in delaying senescence in human lung fibroblasts. J Biol Chem. 2000; 10;275(10):6741–8.

The Lipid Concentrate (GIBCO/INVTTROGEN catalog number 11905-031: Pluronic F-68, 90,000.00 mg/L; Ethyl Alcohol (200 Proof), 100.0 mL/L; Cholesterol, 220.00 mg/L; Tween 80, 2,200.00 mg/L; DL-alpha-Tocopherol acetate, 70.00 mg/L; Stearic acid, 10.00 mg/L; Myristic acid, 10.00 mg/L; Oleic acid, 10.00 mg/L; Linoleic acid, 10.00 mg/L; Palmitic acid, 10.00 mg/L; Palmitoleic acid, 10.00 mg/L; Arachidonic acid, 2.00 mg/L; Linotenic Acid, 10.00 mg/L) is formulated for use in suspension cultured cells grown for recombinant protein production, and allows for serum-free growth that facihtaes purification of the secreted recombinant protein. An ingredient in the Concentrate is Pluronic F68 (BASF, Ludwigshafen, Germany; also called Poloxamer 188 and Lutrol F68, RheothRx, (Glaxo) and Flocor (CytRx)), a non-ionic surfactant included by GIBCO to help dissolve the lipids.

Pluronic F68 also provides a beneficial effect on cell survival in suspension culture (Kilburn D G, Webb F C. The Cultivation of Animal Cells at Controlled Dissolved Oxygen Partial Pressure. Biotechnology and Bioengineering 1968; 10: 801–814), and has been used to protect animal cells from damage caused by shear and the effects of sparging (the aeration bubbles used in bioreactors; Hua et al., Critical Reviews in Biotechnology 1993; 13(4): 305–28). Its use has also been proposed as an intravenous agent for treatment of sickle cell disease and acute vaso-occlusive disorders, and to preserve organs for transplantation (e.g. U.S. Pat. No. 5,990, 241).

Pluronic F68 is a mixture of polyoxyethylene and polyoxypropylene; commercial preparations are mixtures of the polymers with a range of molecular weight from 7680 to 9510. See BASF Technical Bulletin "Pluronic Block Copolymer NF Grades (Poloxamer NF Grades)." U.S. Pat. No. 6,359,014 describes one purification method for commercial preparations of Pluronic F68.

Steinhardt medium may also be used to improve organ transplantation success by perfusing the organ before surgical removal from the donor. This timing is important because we have previously shown that cell membranes must be repaired within 30–90 seconds for a cell to survive a disruption of this protective interface (Steinhardt R A, Bi G, Alderton J M. Cell Membrane Resealing by a Vesicular Mechanism Similar to Neurotransmission. Science 1994; 263: 390–393).

In addition to Steinhardt medium itself, the invention provides methods of making and using the medium, and various kits for making and using the medium. Methods of making the disclosed medium include methods comprising combining the recited ingredients to make the medium; and methods of using the disclosed medium include methods comprising incubating a tissue in the medium, preferably cornea tissue, preferably at 4 degrees C., and preferably for up to at least about 7 days, typically not more than about 21 days.

Kits for using Steinhardt medium include kits comprising a premeasured amount of the disclosed medium; kits comprising a premeasured amount of the disclosed medium and instructions copackaged or associated with the premeasured amount describing use of the medium to preserve a tissue in the medium, preferably cornea tissue, preferably at 4 degrees C., and preferably for up to at least about 7 days, typically not more than about 21 days. Preferred instructions disclose that the medium can provide, or has been shown to provide cold cornea tissue storage for at least about 7 days, preferably for up to about 21 days. The premeasured amounts are preferably contained in a container labeled with the instructions.

Kits for making the disclosed medium include kits comprising premeasured amounts of the recited ingredients, one or more of the ingredients, or a plurality of the ingredients, and recorded instructions copackaged or associated with the premeasured amounts describing the medium and/or how to combine the ingredients to make the medium. The premeasured amounts are preferably contained in a container labeled with the instructions.

EXAMPLES

Evaluations of the endothelial cell layer in bovine corneas in different media. post-incubation survival utility or usefulness for transplantation is defined as less than 3% dying and less than 1.5% missing. Missing cells leave a gap in the layer; calcein-AM staining for esterase activity is used to determine cell health. Transplant surgeons typically use missing cell counts and morphology alone as the index of health and post-incubation survival utility.

TABLE I

Corneas stored in Optisol at 4° C. All experiments were performed double-blind. Conclusion: Optisol does not provide useful tissue beyond 6 days cold storage.

| Days at 4° C. | Percent live | percent dying | percent missing | total cells examined |
|---|---|---|---|---|
| 6 | 98.0 | 2.0 | 0.0 | 892 |
| 6 | 98.6 | 1.0 | 0.3 | 937 |
| 9 | 88.6 | 5.4 | 6.0 | 1338 |
| 9 | 82.3 | 11.6 | 6.1 | 1386 |
| 12 | 67.1 | 16.5 | 16.3 | 1393 |
| 12 | 70.7 | 16.4 | 12.9 | 566 |

TABLE II

Comparison of Steinhardt medium with a defined composition Optisol medium. Corneas stored at 4° C. in Optisol(F) defined media (1) vs. Steinhardt medium. Conclusion: Steinhardt medium stored corneas retain utility at least 21 days.

| Days at 4° C. | Medium | Percent Live | Percent Dying | Percent Missing | Total cells examined |
|---|---|---|---|---|---|
| 4 | Steinhardt | 99.4 (1083) | 0.6 (7) | 0 | 1090 |
| 4 | Steinhardt | 100 (776) | 0 | 0 | 776 |
| 4 | Optisol(F) | 99.0 (576) | 1.0 (6) | 0 | 582 |
| 4 | Optisol(F) | 95.0 (623) | 3.4 (22) | 1.7 (11) | 656 |
| 10 | Steinhardt | 97.8 (840) | 2.0 (17) | 0.2 (2) | 859 |
| 10 | Steinhardt | 100 (635) | 0 | 0 | 635 |
| 10 | Optisol(F) | 92.6 (598) | 5.9 (38) | 1.5 (10) | 646 |
| 10 | Optisol(F) | 91.0 (1154) | 4.9 (62) | 4.1 (52) | 1268 |
| 14 | Steinhardt | 98.7 (869) | 0.9 (8) | 0.4 (3) | 880 |
| 14 | Steinhardt | 99.3 (1216) | 0.7 (9) | 0 | 1225 |
| 14 | Optisol(F) | 85.3 (1039) | 8.4 (102) | 6.3 (77) | 1218 |
| 14 | Optisol(F) | 93.3 (1228) | 4.0 (52) | 2.7 (35) | 1315 |
| 21 | Steinhardt | 96.4 (888) | 2.6 (24) | 1.0 (9) | 921 |
| 21 | Steinhardt | 97.8 (1271) | 1.6 (21) | 0.6 (8) | 1300 |
| 21 | Optisol(F) | 63.6 (743) | 13.5 (158) | 22.9 (268) | 1169 |
| 21 | Optisol(F) | 66.7 (933) | 17.2 (241) | 16.1 (225) | 1399 |

(1) Optisol(F) is formulated as commercial Optisol, but is freshly made and provides better results than commercial Optisol after several days of cornea storage.

Formulation I: Steinhardt Cornea Preservation Medium

| RT Ingredients | Manufacturer | [ ] | MW | for 200 ml |
|---|---|---|---|---|
| Potassium Sulfate $K_2SO_4$ | Mallinckrodt | 5 mM | 174.26 | 0.174 g |
| L-Aspartic Acid | Sigma A-7219 | 110 mM | 133.10 | 2.93 g |
| Magnesium Sulfate | Sigma-1880 | 1.2 mM (1) | 246.5 | 59 mg |
| Calcium Hydroxide | Allied Chemical | 2.0 mM (2) | 74.1 | 29.6 mg |
| Potassium Phosphate, Monobasic $KH_2PO_4$ | Mallinckrodt | 20 mM | 136.1 | 0.544 g |
| HEPES | Sigma H-9136 | 5 mM | 238.3 | 0.238 g |
| EDTA | Sigma EDS | 1 mM | 292.2 | 58.44 mg |
| Taurine | Sigma T-8691 | 20 mM | 125.1 | 0.50 g |
| Zinc Sulfate | Allied Chemical | 1 µM (3) | 287.54 | 200 µl of 2.88 mg/10 ml |

(1) free $Mg^{2+}$: 1.2 mM at 4 C. ; 1.17 mM at 36 C.
(2) free $Ca^{2+}$: 1 mM at 36 C.
(3) free zinc: $1.4 \times 10^{-12}$ M at 36 C. ; $1.7 \times 10^{-12}$ M at 4 C. ; stock is 1 mM (1000×)

Adjust to about pH 7.4 using 1 M KOH.

Add 1M KOH slowly to dissolve the salts completely.

| N-(tert-Butyl) hydroxylamine HCL Refrigerator ingredients: | Aldrich 19,475-1 | 200 μM | 125.6 | 5 mg |
|---|---|---|---|---|
| Dextran | Sigma D-4751(4) | 5% | 68,800 | 10 g |
| N-acetyl-cysteine | Sigma A-9165 | 0.5 mM | 163.2 | 16.3 mg |
| Gentamycin Sulfate | Biowhittaker | | | 20 mg |

Freezer Ingredient:

Creatine Phosphate Calbiochem 2380 5 mM 255.1 0.255 g (4) Takes about 1 hr. to dissolve at RT with stirring Adjust volume to 190 ml. Adjust pH to 7.45. Bring volume to 200 ml. Check osmolarity.=314 mOsmoles. Filter sterilize 0.2μ

Add 1 ml lipid concentrate (Gibco 11905-031(5))/100 ml medium after the medium is aliquoted into the corneal storage vials.

| (5) Lipid Concentrate Composition: | 100× |
|---|---|
| Arachidonic Acid | 2 mg/liter |
| Cholesterol | 0.22 g/liter |
| DL-alpha-Tocopherol Acetate | 70 mg/liter |
| Linoleic, Linolenic, Myristic, Oleic, Palmitoleic, Stearic, and Palmitic Acids | All 10 mg/liter |
| Pluronic F-68 | 100 g/liter |
| Tween 80 | 2.2 g/liter |

Formulation II: Optisol(F) Medium (Prior Art)

| Ingredient; storage. | Source | Quantity |
|---|---|---|
| Medium 199, with Earle's salts, with L-glutamine, with 2,200 mg/L sodium bicarbonate, with 25 mM HEPES; 4 C. | GIBCO 12340-030 | 490 ml |
| Chondroitin sulfate A, sodium salt from bovine trachea; RT. | Calbiochem #230687 | 12.5 g/500 ml |
| Dextran, clinical grade. Av. MW 64.76 K; 4 C. and desiccated. | Sigma D-4751 | 5 g/500 ml |

Stir and intermittently shake the above ingredients at RT and protect from light for several hours or until solids are dissolved. Then add:

| Ingredient | Source | Quantity |
|---|---|---|
| Choline, Chloride salt; RT. | Sigma C-1879 | 0.5 mg/500 ml |
| Folic acid; RT. | Sigma F-8758 | 0.5 mg/500 ml |
| i-Inositol myo-inositol; RT. | Sigma I-7508 | 1 mg/500 ml |
| Inosine; RT. | Sigma I-4125 | 5 mg/500 ml |
| L-Asparagine; RT, desiccated. | Aldrich #A9, 300-3 | 6.6 mg/500 ml |
| Riboflavin; RT. | Sigma R-4500 | 0.05 mg/500 ml |
| Nicotinamide; RT. | Sigma-0636 | 0.5 mg/500 ml |
| L-glutamine; RT. | Sigma G-3126 | 100 mg additional/500 ml |
| Vitamin $B_{12}$; 4 C. and desiccated. | Sigma V-6629 | 0.68 mg/500 ml |
| D-Pantothenic acid; 4 C. and desiccated. | Sigma P-5155 | 0.5 mg/500 ml |
| Adenosine, free base 4 C. and desiccated. | Sigma A-9251 | 0.75 mg/500 ml |
| Alpha-tocopherol phosphate, disodium salt; 4 C and desiccated. | Sigma T-2020 | 25 mg/500 ml |
| Pyridoxal HCl; −20 C. and desiccated. | Sigma P-9130 | 0.5 mg/500 ml |
| Gentamycin sulfate; 4 C. liquid stock @ 50 mg/ml | BioWhittaker # 17-518Z | 50 mg/500 ml |
| Sodium pyruvate liquid; 4 C. and protected from light; yields 1 mM final concentration. | GIBCO #11360-070 | 5 ml stock/500 ml |
| 2-mercaptoethanol liquid stock; 4 C. Thiamine, HCl Sigma T-1270; rapidly destroyed above pH 5.5; 1000x stock in MES = 2[N-Morpholino] ethane Sulfonic Acid buffer Sigma-8250, pH 5.5. Yields 0.5 mg Thiamine, HCl/500 ml Add just before cornea is placed in the medium. | GIBCO BRL #21985-023 | 0.45 ml/500 ml 1 microliter/ml |

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cornea preservation medium comprising in sterile solution the following ingredients in final concentration:
   5 mM potassium sulfate,
   110 mM L-aspartic acid,
   1.2 mM magnesium sulfate, 2.0 mM calcium hydroxide,
20 mM potassium phosphate monobasic,
5 mM N-2-hydroxyethylpiperazine-N'-2-ethanesulfonic acid,
1 mM ethylenediaminetetraacetic acid,
20 mM taurine,
1 microM zinc sulfate,
200 microM N-(tert-butyl) hydroxylamine HCL,
5.5% w/v dextran, molecular weight 60,000–90,000,
0.5 mM N-acetyl-cysteine,
0.02% w/v gentamycin sulfate,
5 mM creatine phosphate,
1% v/v of a lipid concentrate which contains
    90,000 mg/L Pluronic F-68,
    100 ml/L ethyl alcohol,
    220 mg/L cholesterol,
    2,200 mg/L Tween 80,
    70 mg/L DL-alpha-tocopherol acetate,
    10 mg/L stearic acid,
    10 mg/L myristic acid,
    10 mg/L oleic acid,
    10 mg/L linoleic acid,
    10 mg/L palmitic acid,
    10 mg/L palmitoleic acid,
    2 mg/L arachidonic acid,
    10 mg/L linolenic acid;
and is adjusted with 1 M KOH to pH 7.45 and having an osmolarity of 310–320 mOsmoles.

2. A kit for preserving tissue comprising:
a premeasured amount of the preservation medium of claim 1.

3. A kit for preserving tissue comprising:
a premeasured amount of the preservation medium of claim 1, and
recorded instructions copackaged or associated with the premeasured amount describing use of the medium to preserve a tissue.

4. A kit for making the preservation medium of claim 1, comprising:
premeasured amounts of a plurality of the ingredients; and
recorded instructions copackaged or associated with the premeasured amounts describing how to combine the ingredients to make the medium.

5. A method of making the preservation medium of claim 1, comprising the step of:
combining the recited ingredients to make the medium.

6. A method of using the preservation medium of claim 1, comprising the step of:
incubating a tissue in the medium.

7. A method of using the preservation medium of claim 1, comprising the step of:
incubating a tissue in the medium; and
verifying post-incubation survival utility of the tissue.

8. A method of using the preservation medium of claim 1, comprising the step of:
incubating a tissue in the medium at 4 degrees C.

9. A method of using the preservation medium of claim 1, comprising the step of:
incubating a tissue in the medium at 4 degrees C.; and
verifying post-incubation survival utility of the tissue.

10. A method of using the preservation medium of claim 1, comprising the step of:
incubating a tissue in the medium at 4 degrees C. for between 7 and 21 days.

11. A method of using the preservation medium of claim 1, comprising the step of:
incubating a tissue in the medium at 4 degrees C. for between 7 and 21 days; and
verifying post-incubation survival utility of the tissue.

12. A method of using the preservation medium of claim 1, comprising the step of:
incubating a cornea tissue in the medium at 4 degrees C. for between 7 and 21 days.

13. A method of using the preservation medium of claim 1, comprising the step of:
incubating a cornea tissue in the medium at 4 degrees C. for between 7 and 21 days; and
verifying post-incubation survival utility of the tissue.

* * * * *